US012591258B2

(12) United States Patent
Zapalac

(10) Patent No.: US 12,591,258 B2
(45) Date of Patent: Mar. 31, 2026

(54) SYSTEM AND METHOD TO MEASURE TEMPERATURE AND GENERATE HEAT USING A RESISTIVE MATERIAL

(71) Applicant: Varian Medical Systems, Inc., Palo Alto, CA (US)

(72) Inventor: Kenneth Wayne Zapalac, Cedar Park, TX (US)

(73) Assignee: Varian Medical Systems, Inc., Palo Alto, CA (US)

( * ) Notice: Subject to any disclaimer, the term of this patent is extended or adjusted under 35 U.S.C. 154(b) by 613 days.

(21) Appl. No.: 18/169,636

(22) Filed: Feb. 15, 2023

(65) Prior Publication Data

US 2024/0272660 A1 Aug. 15, 2024

(51) Int. Cl.
| | |
|---|---|
| *G05D 23/24* | (2006.01) |
| *G01K 3/00* | (2006.01) |
| *G01K 7/16* | (2006.01) |
| *H05B 3/06* | (2006.01) |

(Continued)

(52) U.S. Cl.
CPC ......... *G05D 23/2401* (2013.01); *G01K 3/005* (2013.01); *G01K 7/16* (2013.01); *H05B 3/06* (2013.01); *A61B 2018/00577* (2013.01); *A61B 2018/00702* (2013.01); *A61B 2018/00714* (2013.01); *A61B 2018/00815* (2013.01); *A61B 2018/00827* (2013.01); *A61B 2018/0262* (2013.01); *A61B 2018/0293* (2013.01); *G01K 2219/00* (2013.01)

(58) Field of Classification Search
CPC ... G05D 23/2401; G01K 7/16; G01K 2219/00
See application file for complete search history.

(56) References Cited

U.S. PATENT DOCUMENTS

| | | | |
|---|---|---|---|
| 3,948,269 A | 4/1976 | Zimmer | |
| 4,202,336 A | 5/1980 | van Gerven | |

(Continued)

FOREIGN PATENT DOCUMENTS

| | | |
|---|---|---|
| EP | 3213708 B1 | 2/2019 |
| EP | 2904986 B1 | 7/2022 |

(Continued)

OTHER PUBLICATIONS

Parthasarathy et al., "Development of educational model of power compensated differential scanning calorimeter (PC-DSC)", CIST, vol. 9, Nov. 27, 2020, pp. 59-70. (Year: 2020).*

(Continued)

*Primary Examiner* — Lorne E Meade
(74) *Attorney, Agent, or Firm* — Morgan, Lewis & Bockius LLP; Manita Rawat

(57) ABSTRACT

A heating system includes a power supply that applies a first voltage to a sense resistor in series with a resistive heating material during a first time period; and a controller that determines a temperature of the resistive heating material based on a current through the sense resistor and a second voltage across the resistive heating material during the first time period. Additionally, the controller commands the power supply to provide a third voltage to the resistive heating material during a second time period, and the third voltage is based on the temperature of the resistive heating material.

19 Claims, 3 Drawing Sheets

(51) Int. Cl.
   *A61B 18/00*        (2006.01)
   *A61B 18/02*        (2006.01)

(56) References Cited

U.S. PATENT DOCUMENTS

| | | | | |
|---|---|---|---|---|
| 7,846,154 | B2 * | 12/2010 | Bliweis | A61B 18/082 |
| | | | | 606/24 |
| 7,938,822 | B1 * | 5/2011 | Berzak | A61B 18/02 |
| | | | | 606/22 |
| 9,675,402 | B2 | 6/2017 | Yasunaga | |
| 9,833,278 | B2 | 12/2017 | Yasunaga | |
| 9,895,184 | B2 | 2/2018 | Baust | |
| 10,543,035 | B2 | 1/2020 | Sutermeister et al. | |
| 11,051,879 | B2 * | 7/2021 | Hasegawa | A61B 18/1492 |
| 2006/0122590 | A1 | 6/2006 | Bliweis et al. | |
| 2018/0106686 | A1 * | 4/2018 | Furtner | G01K 7/16 |

| | | | |
|---|---|---|---|
| 2018/0296265 | A1 | 10/2018 | Hasegawa et al. |
| 2019/0117288 | A1 | 4/2019 | Littrup et al. |
| 2019/0142492 | A1 | 5/2019 | Kollmann et al. |
| 2022/0369931 | A1 | 11/2022 | Kollmann et al. |

FOREIGN PATENT DOCUMENTS

| | | |
|---|---|---|
| WO | 2011142909 A1 | 11/2011 |
| WO | 2019077508 A1 | 4/2019 |
| WO | 2020163854 A1 | 8/2020 |
| WO | 2024173023 A1 | 8/2024 |

OTHER PUBLICATIONS

International Search Report and Written Opinion issued for PCT International Application No. PCT/US2024/013164 dated Jun. 6, 2024, 15 pages.

* cited by examiner

200

300

304             302        340

440

442

410

422

424           420

SYSTEM AND METHOD TO MEASURE TEMPERATURE AND GENERATE HEAT USING A RESISTIVE MATERIAL

FIELD

The present disclosure relates to a system and method to measure temperature and generate heat using a conductive resistive material to heat an adjacent object. The system and method can be used in a cryoablation probe.

BACKGROUND

Electrically conductive and resistive materials can be used as heating elements. An electrically conductive material or resistive element can convert electrical energy to heat energy. That is, as a property, the electrically conductive material gets hot when electricity flows through it. For example, a voltage potential can be applied to an electrically conductive material converting the voltage into heat. The power of heating generated by an electrical conductor by a voltage equals its resistance divided into the square of the voltage.

The resistive material can be attached to an article or located such that the heat generated by the resistive material can be intentionally transferred to heat up the article. The resistive material can take any of several forms including being a sheet, a foil, a block, a filament, a coiled wire, etc. and be made from an electrical conductor such as metal, metal oxide, alloy, metalized ceramic, or the like.

Many conventional designs try to regulate the amount of power that is being delivered to the resistive heating material. This method works if the thermal transfer rate is known and is consistent. If the thermal transfer rate changes quickly, then there is a risk of overheating the resistive heater to the point that the resistive heating material and any associated electrical insulation degrades or is destroyed. The temperature of the resistive heating material (i.e., heater) is often measured with some form of additional sensor attached to or located adjacent to the resistive heater. For example, the sensor component can be a thermocouple, a resistive temperature detector (RTD), or a thermistor.

There exists a need, therefore, for improved resistive heating systems and methods to measure ambient temperature without a separate sensor component and to control the temperature of the resistive heating material while power is being applied so that maximum heat can be delivered without severely degrading or burning up the resistive heating material and any electrical insulating material that is being used to electrically isolate the resistive heating material from its surroundings.

SUMMARY

This section provides a general summary of the disclosure, and is not a comprehensive disclosure of its full scope or all of its features.

Embodiments of the present disclosure solve at least two problems. The first is to measure ambient temperature using a resistive heating material without a separate sensor. The second is to control the temperature of that resistive heating material while power is being applied so that maximum heat can be delivered without severely degrading or burning up the resistive heating material and any electrical insulating material used with the resistive heating material.

A heating system according to an embodiment includes a power supply that applies a first voltage across a sense resistor in series with a resistive heating material during a first time period; and a controller that determines a temperature of the resistive heating material based on a current through the sense resistor and a second voltage across the resistive heating material during the first time period.

In an aspect, the controller commands the power supply to provide a third voltage across the resistive heating material during a second time period. A resulting current through the resistive heating material is a function of the temperature of the resistive heating material and the third voltage.

In an aspect, a resistance of the resistive heating material is a function of the temperature of the resistive heating material.

The heating system can further include a first analog to digital converter that sends a signal representing the current through the sense resistor to the controller; and a second analog to digital converter that sends a signal representing the second voltage to the controller.

The heating system can further include a first switch between the power supply and the sense resistor and a second switch between the power supply and the resistive heating material, wherein the first switch is closed during the first time period, and the second switch is closed during the second time period.

In an aspect, the power supply is pulse width modulated during the second time period.

In an aspect, the first voltage is less than the second voltage.

In an aspect, the first time period is less than the second time period.

In an aspect, the resistive heating material heats a portion of a cryoablation probe. In an aspect, the resistive heating material is located at a tip of the cryoablation probe and heats one of a cryo-fluid and the cryoablation probe. In an aspect, the resistive heating material is a coil located at a tip of the cryoablation probe.

A method of heating, according to an embodiment includes applying a sense voltage to a sense resistor and a resistive heater; determining a current through the sense resistor; determining a voltage across the resistive heater; calculating a resistance of the resistive heater based on the current and the voltage; and determining a temperature of the resistive heater based on the resistance of the resistive heater.

The method can further include upon a condition that the temperature of the resistive heater is at or below a target temperature, (i) determine a heating voltage to be delivered to the resistive heater and (ii) delivering the heating voltage to the resistive heater, and upon a condition that the temperature of the resistive heater is above the target temperature, repeating the steps of the method.

In an aspect, some steps are performed within a first time period, and delivering the heating voltage is performed within a second time period.

In an aspect delivering the heating voltage to the resistive heater includes modulating a pulse width of the heating voltage.

The method can further include determining a heating voltage to be delivered to the resistive heater, and delivering the heating voltage to the resistive heater.

In an aspect, a non-transitory computer-readable medium includes executable instructions that when executed by a processor cause the processor to perform the steps of the method.

A system to perform heating, according to an embodiment includes a sensing circuit; a heating circuit; and a controller circuit; wherein the controller circuit controls power to the sensing circuit to determine a resistance value of a heater that is in both the sensing circuit and the heating circuit.

In an aspect, a temperature of the heater is determined based on the resistance value of the heater.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

DETAILED DESCRIPTION

Figure 1:
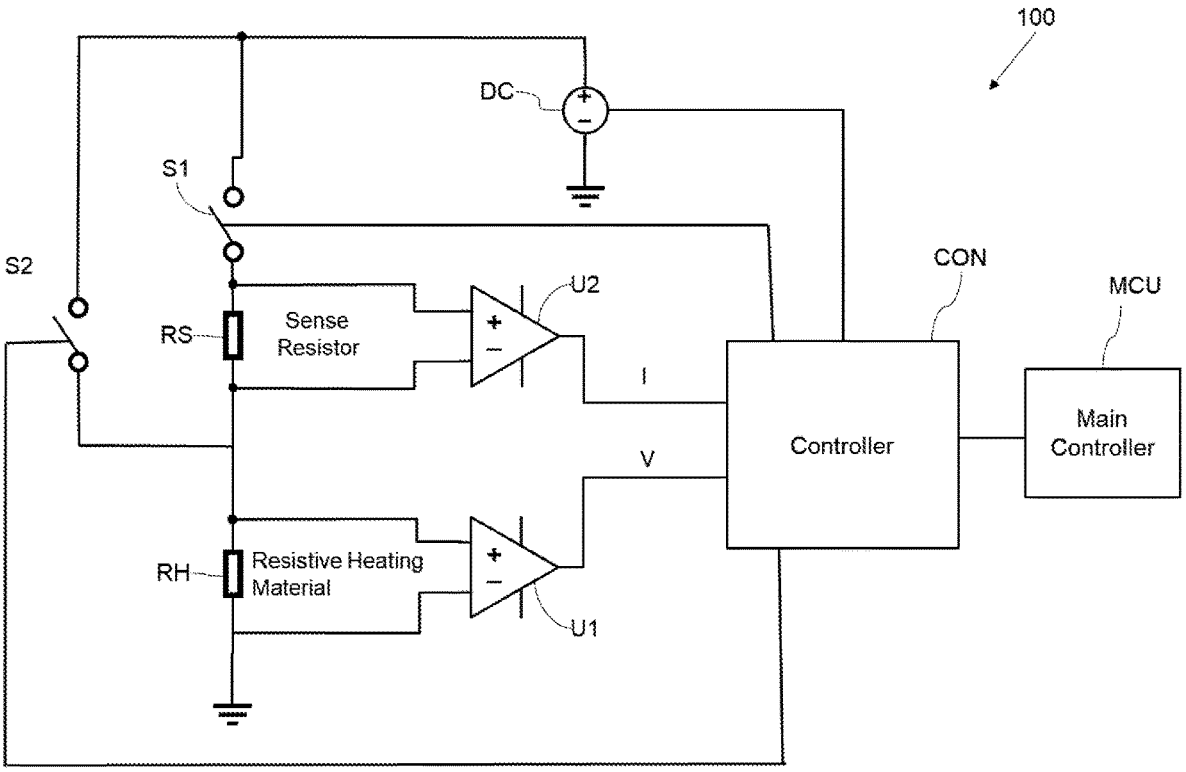
FIG. 1 is a diagram illustrating an example heating and measurement system according to an embodiment of the present disclosure.

Example embodiments will now be described more fully with reference to the accompanying drawings.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

Embodiments of the present disclosure solve the problem of requiring a separate temperature sensor component by measuring the ambient temperature using a resistive heating material. Additionally, embodiments control the temperature of the resistive heating material while power is being applied to the resistive heating material so that overheating does not occur.

Embodiments of the present disclosure deliver discreet packets of controlled electrical energy to the resistive heating material. After each packet of electrical energy is delivered, the disclosed embodiments use a relatively low power method to measure the resistance value of the resistive heating material. Because the resistance of the resistive heating material is directly related to the temperature of the resistive heating material, a calculation can be performed to determine the temperature of the resistive heating material. The disclosed embodiments use the measured resistance to determine the amount of energy to be delivered in the following packet. This process repeats multiple times per second. This process ensures that the resistive heating material is maintained at a temperature level that delivers maximum heating while also ensuring that the resistive heating material and any electrical insulation are not being damaged. If only the temperature needs to be measured, the same process is carried out except no energy is delivered during the heating phase.

FIG. 1 is a schematic diagram illustrating an example heating and measurement system 100 in accordance with an embodiment of the present disclosure. FIG. 1 shows that the heating and measurement system 100 can include a sensing circuit and a heating circuit where the circuits can include direct current (DC) power supply DC, two switches S1 and S2, a sense resistor RS in series with a resistive heating material RH, two analog-to-digital converters (ADC) U1 and U2, a controller CON, and a main controller MCU connected together in a circuit.

The power supply DC can provide a fixed voltage such as up to +24 volts or any other suitable voltage where the period or duty cycle can be adjustable. In one aspect the power supply DC includes voltage regulation to provide a second voltage that is less than the fixed voltage. For example, the fixed voltage can be +24 volts that is regulated down to +12 volts. In one aspect, the power supply DC can be programmable such that it can provide a voltage that is adjustable over a range and output for a period of time. In another aspect, the power supply DC can be programmable such that both the voltage and the output time period can be adjustable.

The switches S1 and S2 can be field effect transistors (FETs) with gate voltages controlled by the controller CON to turn on and off the transistor switches S1, S2. As shown, switch S1 can be in series with the power supply DC, the sense resistor RS, and the resistive heating material RH in the sensing circuit. Switch S2 can be in series with the power supply DC and the resistive heating material RH in the heating circuit.

Analog-to-digital converter U1 can be connected to provide a value representing a voltage potential across the resistive heating material RH to the controller CON. Analog-to-digital converter U2 can be connected to provide a value representing a current through the sense resistor RS to the controller CON.

The controller CON can be programmed to sense or control the power supply DC, control the switches S1, S2, and receive input from the ADCs U1, U2. The resistive heating material RH is meant to provide heat for another object or article within a greater system, an example of which is describe below, and the controller CON can be connected to a main controller MCU of that system. The controller CON can be a processor, microcontroller, PLC, data acquisition unit, or any other suitable control circuit. The main controller MCU can be a personal computer, central processing unit, or network of computers and include an associated memory.

The controller CON is operable to receive measurement signals from the ADCs U1, U2 and to control, change, or adjust operating parameters of the system 100. For example, the controller CON can be operable to control the voltage/power to the resistive heating material RH. The controller CON can change, adjust, or control the voltage and duty cycle of the power delivered to the resistive heating material RH. In an aspect, the controller CON can control a plurality of resistive heating materials and/or control a multiplexer that simultaneously operates a plurality of resistive heating materials as heaters.

The main controller MCU can be a personal computer, central processing unit, or network of computers that includes a processor and a memory. The main controller MCU can be more powerful than the controller CON such that it is faster, more flexible, includes more features, and is generally more capable. The memory in the main controller MCU can include a non-transitory computer readable medium that can store an executable program to provide calculations and functions to operate the heating and measurement system 100.

Figure 2:
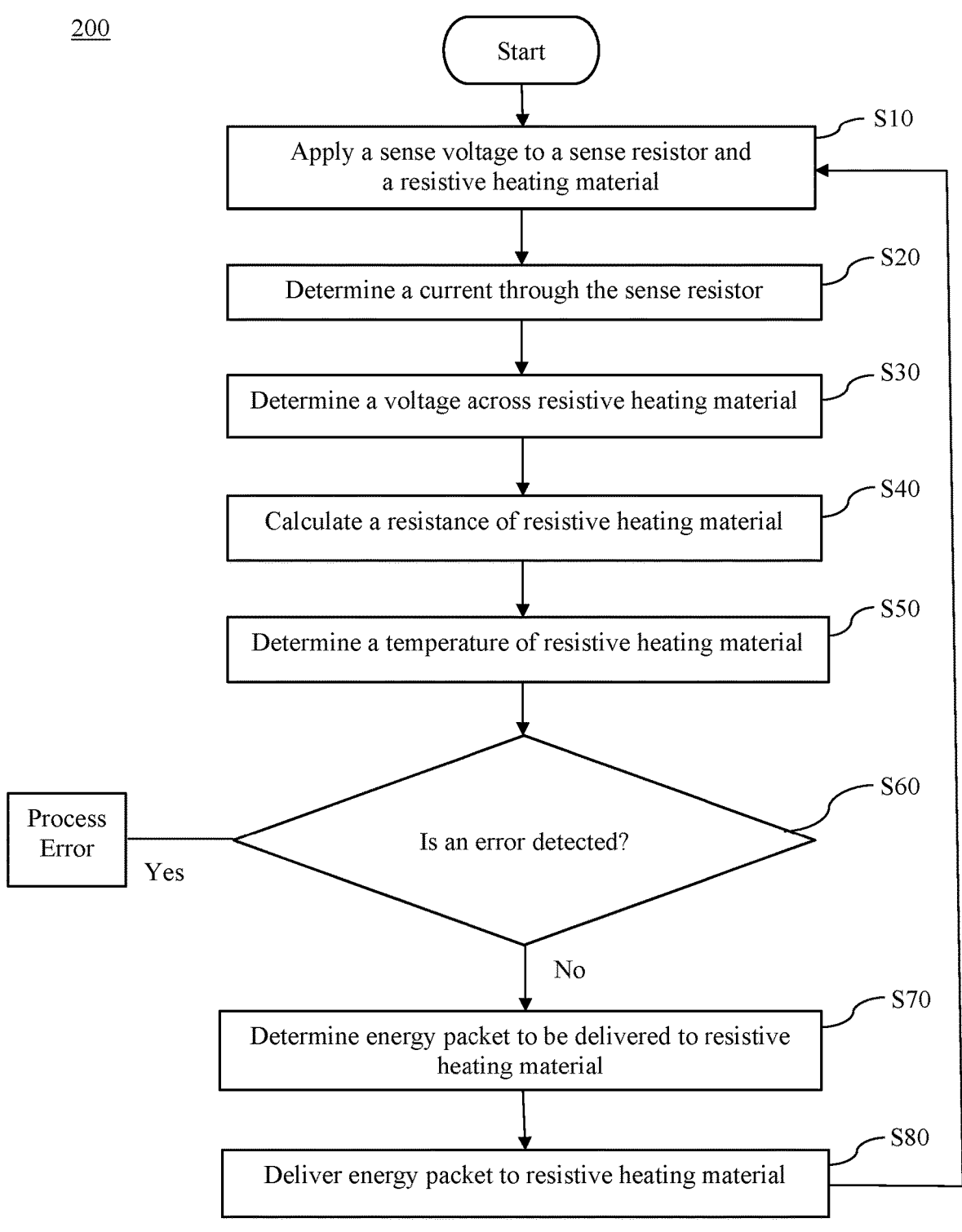
FIG. 2 is a flow chart illustrating an example method of heating in accordance with an embodiment of the present disclosure.

FIG. 2 is a flow diagram representing steps of a method 200 to operate the heating and measurement system 100 according to an embodiment. The disclosed embodiments measure and control the temperature of the resistive heating material while providing the amount of power being delivered to it to control the heating temperature. This permits the temperature of the resistive heater material to be controlled and maintained at a level that delivers a predetermined level of heating power while maintaining the temperature of the resistive heater material below the point where the resistive heating material or electrical insulation associated with the resistive heating material or adjacent heated article start to degrade.

The method, during a first period measurement phase, provides a relatively low sensing voltage (i.e., lower than a heating voltage), measures a current through the sense resistor RS and the resistive heating material RH, measures a voltage across the resistive heating material RH, calculates a resistance value of the resistive heating material RH based on the current and voltage measured, determines a temperature of the resistive heating material RH based on the calculated resistance value, and determines a heating voltage to be applied. During a second period heating phase, the method provides the heating voltage to the resistive heating material RH. The first and second periods can be arranged so that the resistive heating material RH reaches and maintains a target temperature within a tolerance or hysteresis value. The target temperature can be any temperature suitable for the heating application.

The disclosed embodiments use a relatively low power level while the resistance of the resistive heating material RH is being measured. This allows for a very accurate temperature to be calculated because the low power level does not contribute to significate heating of the resistive heating material. The embodiments can act as a temperature indicator both when being used for heating and when not being used for heating.

The embodiments provide fault detection. Stopping the heating power delivery multiple times per second during the measurement phase allows the control system to automatically stop heating power delivery if a fault condition occurs. The heating power delivery will not restart until the control system issues a new heating level command. If the temperature measuring circuitry does not return a resistance measurement or if a bad measurement is returned, the control system will not issue a new heating level command.

By stopping the heating power delivery multiple times per second and measuring the resistance of the resistive heating material using a relatively low power level, many different types of resistive heater materials can easily be controlled by the disclosed embodiments. The control system can use the resistive heater material's resistance versus temperature characteristics to determine how the heating power level should be controlled to reach a target temperature without overheating.

In the heating and measurement system 100, it is contemplated that the resistance of the sense resistor RS is known and the resistance of the resistive heating material RH is a function of its temperature. The resistance of the sense resistor can be relatively high, in the range of 10K to 50K Ohms, so that the current I is relatively low. For example, the resistance of the sense resistor RS can be 20K Ohms. Depending on the material, the resistance of the resistive heating material RH can vary nonlinearly over a temperature range.

Upon initiating the method, at step S10 the controller can close switch S1, open switch S2, and command the power supply DC to apply a sense voltage through the sense resistor RS and the resistive heating material RH. The sense voltage can be a relatively lower voltage than a heating voltage. For example, the sense voltage can be +12 volts and the heating voltage can be +24 volts, although any suitable voltages are possible.

At step S20, the controller CON reads a signal from the ADC U2. Depending on the performance level of the controller CON, the controller CON can use the signal to determine the current I flowing through the sense resistor RS or the controller CON can send the raw signal from the ADC U2 to the main MCU so that the main MCU can determine the current I.

At step S30, the controller CON reads a signal from the ADC U1. Depending on the performance level of the controller CON, the controller CON can use the signal to determine the voltage V across the resistive heating material RH or the controller CON can send the raw signal from the ADC U1 to the main MCU so that the main MCU can determine the voltage V.

At step S40, the main controller MCU receives values corresponding to the current I and the voltage V from the controller CON and calculates the resistance value of the resistive heating material RH.

At step S50, the main controller MCU determines the temperature of the resistive heating material RH based on the calculated resistance value. This determination can be made by using a scaling factor, an algorithm that characterizes the resistance-temperature property of the resistive heating material RH, or a look-up table stored in memory. The look-up table would include records of temperature that corresponds to a resistance value for the resistive heating material RH.

At step S60, the main controller MCU compares the temperature of the resistive heating material RH to a predetermined target temperature. If the temperature of the resistive heating material is outside of the predetermine target limit there could be an error condition that needs to be addressed (i.e. a broken heater wire, a shorted heater wire, a runaway heating condition, etc.). The main controller MCU can process the error condition and provide protective measures such as alerting an operator, shutting down the power supply DC, or any other suitable action. In such a case, the operator can be instructed to take a precautionary action. If the temperature of the resistive heating material RH is within reasonable limits, the method can proceed to step S70.

At step S70, the main controller MCU determines an energy packet (i.e., a heating power for a period of time, the power being equal to the heating voltage squared divided by the resistance of the resistive heating material RH) in watts-sec to be delivered to the resistive heating material RH and forwards a command to the controller CON to control the power supply DC to deliver that energy packet. If the temperature of the resistive heating material RH is below the target temperature, the value of the next energy packet can be increased. If the temperature of the resistive heating material RH is at the target temperature within a suitable temperature window (e.g., ±5° C.) the next energy packet can be the same value as the previous energy packet. If the temperature of the resistive heating material RH is above the target temperature, the value of the next energy packet can be reduced. If the temperature of the resistive heating material RH is much higher than the target temperature, the next energy packet size should be reduced to zero to minimize any further temperature increase and possible damage to the heater coil and/or article it is heating.

Performance of steps S10 through S70 are completed as quickly as possible to minimize the time of no heat delivery. Hardware selection and cost tradeoffs will dictate the maximum time needed to make accurate measurements with the ADCs and for the MCU to calculate the value of the new energy packet. For example, the time for completing steps S10 through S60 can be 30 msec. It has been found that this is enough time to allow for the electronics to settle and for the ADCs U1, U2 to make the measurements. If faster ADCs and associated hardware are used, this time could be reduced to less than 2 msec.

At step S80, the controller CON opens switch S1, closes switch S2, and commands the power supply DC to output the energy packet determined in step S70 to the resistive heating material RH. The amount of heating energy or power delivered can be changed by varying the heating voltage (i.e., amplitude modulation) and/or the period of time for which the heating voltage can be applied (i.e., pulse width modulation).

In one aspect, the power supply DC outputs a fixed heating voltage (e.g., +24 volts) for different amounts of time within the heating time period. The heating time period can be any suitable length. For example, the heating time period can be 250 msec. For example, the 250 msec heating time period can be divided into 25 cycles of 10 msec each. Within each of the 10 msec cycles, the heating voltage can be applied for all or a portion of the 10 msec cycle. In an aspect, pulse width modulation of the heating voltage can be performed by turning on and off switch S2. In another aspect, the power supply DC can output a voltage value within its operating range for a set period of time.

Example

In an embodiment, a heating and measurement system can be incorporated into a cryoablation probe used for providing cryoablation treatments at or near target tissue in a patient. A cryoablation system can include a controller and an extremely cold cryo-fluid (liquid, gas, or mixed phase) that can be passed through a cryoablation probe in thermal contact with the target tissue. The cryoablation system in combination with the cryoablation probe can be configured in various suitable manners such as a Joules-Thompson cryoablation system, critical or near-critical cryoablation system, or others. During cryoablation treatments, heat from the target tissue passes from the tissue through the cryoablation probe and into the fluid that removes heat from the target tissue. This removal of heat causes the target tissue to freeze, resulting in the destruction of the target tissue. The cryo-fluid or tip of the cryoablation probe can also be heated subsequent to the freezing cycle. This heating can thaw a portion of the frozen tissue to permit the cryoablation probe to be more easily removed from the frozen tissue. The heating can also be raised enough to be used to coagulate blood or cauterize tissue in instances of bleeding at the cryoablation site. It is desirable to reduce or minimize bleeding that can occur during cryoablation treatments to minimize the impact of the bleeding to the health of the patient.

Figure 3:
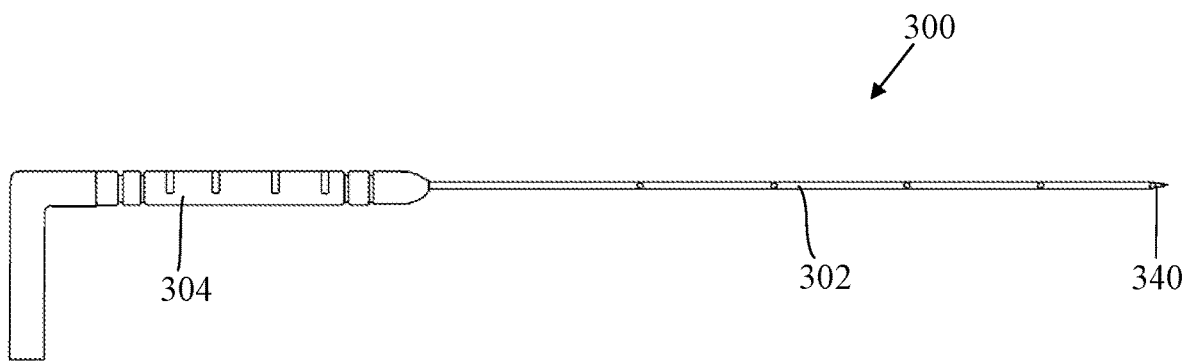
FIG. 3 is a side view of an example of a cryoablation probe.

FIG. 3 is an example of a cryoablation probe 300. As shown, the cryoablation probe 300 can include a handle 304 and a needle 302. The needle 302 can extend from the handle 304 to a distal end 340 or tip. The handle 304 and the needle 302 can be used to enclose various conduits, wires, or other pathways that can allow a cryo-fluid and/or other electrical paths to pass from the needle 302 to a controller and/or the main controller of the cryoablation system.

Figure 4:
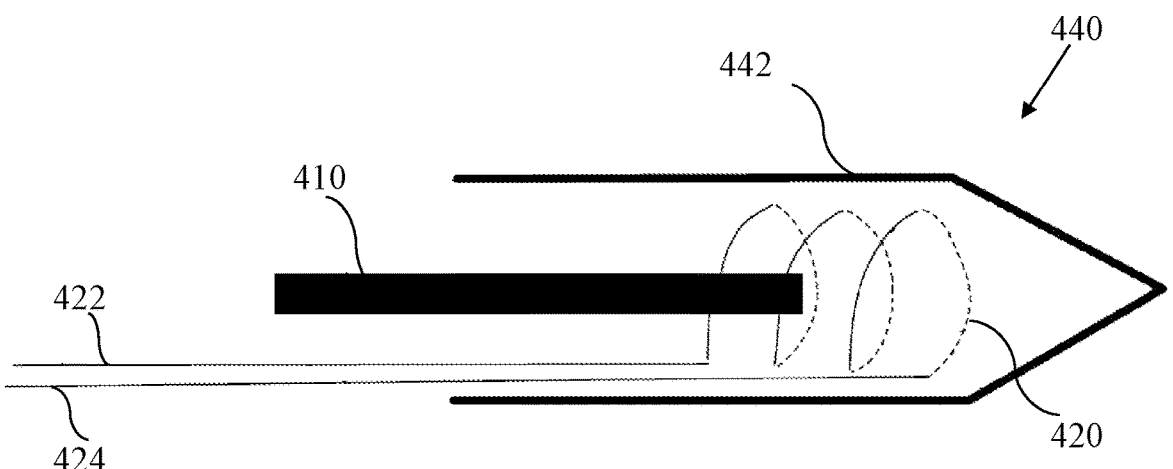
FIG. 4 is a diagram of a tip of a cryoablation probe including a heater.

FIG. 4 is an example of a distal end 440 of a cryoablation probe. As shown, a heater 420 can be positioned in thermal communication with a supply conduit 410. In this manner, the heater 420, when activated, can heat cryo-fluid that is moving through the supply conduit 410. In the example shown, the heater 420 can be configured as a resistive heating element that include a plurality of coils that are wrapped around the supply conduit 410. The heater 420 can be coupled to a heating and measurement system via the leads 422 and 424. The leads 422, 424 can be copper wires covered with a jacket of electrical insulating material. When heating power is provided to the heater 420 via the leads 422 and 424, the heater 420 can heat up and transfer heat to the cryo-fluid moving through the supply conduit 410. In another aspect, the heater 420 can be in contact with or otherwise directly heat the cryoablation probe.

Components of the heating and measurement system other than the heater 420 can be included in a separate circuit assembly as part of the cryoablation system controller.

The amount of heat that is transferred to the fluid in the supply conduit 410 or the cryoablation probe can be controlled by a main controller via the heating system to heat the fluid to a predetermined temperature or to a predetermined temperature range. The heater 420 can be controlled via a power signal that is provided to the heater 420. As described above, a predetermined power profile can be delivered and modified to heat the fluid as desired using methods including pulse width modulation (PWM), a duty cycle, amplitude modulation, and/or predetermined current and voltage profiles.

The distal end 440 of the needle can have various structures that can allow the cryo-fluid in the input conduit 410 to heat the needle. One example structure of the distal end 440 is shown in FIG. 4. In this example, the supply conduit 410 is positioned in a shell 442 of the needle. The shell 442 can be shaped as a cylindrical member that terminates at the tip. The shell 442 can define a cavity into which the supply conduit 410 can be located. The supply conduit 410 can be coupled to a fluid supply to allow the cryo-fluid to flow through the supply conduit 410 to the distal end 440 of the needle. The cryo-fluid can then exit the supply conduit 410 proximate the tip of the needle and contact the shell 442. The cryo-fluid can then flow back toward the handle and fluid supply. In this manner, thermal energy can be exchanged between the cryo-fluid and the shell 442. This allows the needle to be heated or cooled as desired. In an aspect, the heater 420 can be configured to transfer heat directly to the outer shell 442 of the needle at the distal end 440.

During a heating cycle of the cryoablation probe, a cryo-fluid (in a liquid, gas, or mixed form) can be passed through the supply conduit 410 while the heater 420 is activated. The heater 420 can heat the cryo-fluid as it moves past the heater 420. The heated cryo-fluid can move into the needle toward the distal end 440 through the supply conduit 410. The heated cryo-fluid can contact the shell 442 to heat the tissue, ice, or area surrounding the distal end 440 of the needle. In this manner, the tissue, ice, or other surrounding area of the needle can be heated as desired. For example, the heater 420 can be heated to about a body temperature. For example, the heater 420 can be heated to be within a temperature range of about 30° C. to 37° C. to melt ice formed at the target tissue. For example, the heater 420 can be heated to be within a temperature range of about 80° C. to 100° C. to cauterize tissue. The heated cryo-fluid can then flow away from the distal end 440 along a return pathway and back through the supply conduit 410 to the fluid source.

The heater 420 can be made of a resistive heating material that can heat when electrical power is passed to the heater 420 via the leads 422, 424. The amount of thermal energy that is passed from the heater 420 to the cryo-fluid or cryoablation probe can be controlled by controlling the power provided to the heater 420 via the leads 422, 424 as discussed above. The leads 422, 424 can be coupled to a power supply. In other examples, the heater 420 can include a magnetic coil heater, a fiber laser heater, or the like.

The above-described embodiments of the present disclosure can be implemented in any of numerous ways. For example, the embodiments can be implemented using hardware, software, or a combination thereof. When implemented in software, the software code can be executed on any suitable computer, processor, or collection of processors, whether provided in a single computer or distributed among multiple computers. Such processors can be implemented as integrated circuits, with one or more processors in an integrated circuit component. Though, a processor can be implemented using circuitry in any suitable format.

Additionally, or alternatively, the above-described embodiments can be implemented as a non-transitory computer readable storage medium embodied thereon a program executable by a processor that performs a method of various embodiments.

Also, the various methods or processes outlined herein can be coded as software that is executable on one or more processors that employ any one of a variety of operating systems or platforms. Additionally, such software can be written using any of a number of suitable programming languages and/or programming or scripting tools, and also can be compiled as executable machine language code or intermediate code that is executed on a framework or virtual machine. Typically, the functionality of the program modules can be combined or distributed as desired in various embodiments.

Also, the embodiments of the present disclosure can be embodied as a method, of which an example has been provided. The acts performed as part of the method can be ordered in any suitable way. Accordingly, embodiments can be constructed in which acts are performed in an order different than illustrated, which can include performing some acts concurrently, even though shown as sequential acts in illustrative embodiments.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A heating system, comprising:
a power supply that applies a first voltage across a sense resistor in series with a resistive heating material during a first time period;
a controller that determines a temperature of the resistive heating material based on a current through the sense resistor and a second voltage across the resistive heating material during the first time period;
a first switch between the power supply and the sense resistor; and
a second switch between the power supply and the resistive heating material, wherein the first switch is closed during the first time period, and during a second time period, the first switch is opened and the second switch is closed.

2. The heating system of claim 1, wherein the controller commands the power supply to provide a third voltage across the resistive heating material during the second time period, and a resulting current through the resistive heating material is a function of the temperature of the resistive heating material and the third voltage.

3. The heating system of claim 2, wherein a resistance of the resistive heating material is a function of the temperature of the resistive heating material.

4. The heating system of claim 2, wherein the power supply is pulse width modulated during the second time period.

5. The heating system of claim 1, further comprising:
a first analog to digital converter that sends a signal representing the current through the sense resistor to the controller; and
a second analog to digital converter that sends a signal representing the second voltage to the controller.

6. The heating system of claim 1, wherein the first voltage is less than the second voltage.

7. The heating system of claim 1, wherein the first time period is less than the second time period.

8. The heating system of claim 1, wherein the resistive heating material heats a portion of a cryoablation probe.

9. The heating system of claim 8, wherein the resistive heating material is located at a tip of the cryoablation probe and heats one of a cryo-fluid and the cryoablation probe.

10. The heating system of claim 8, wherein the resistive heating material is a coil located at a tip of the cryoablation probe.

11. A method of heating, comprising:
applying a sense voltage to a sense resistor in series with a resistive heater during a first time period;
determining a current through the sense resistor during the first time period;
determining a voltage across the resistive heater during the first time period;
calculating a resistance of the resistive heater based on the current and the voltage during the first time period;
determining a temperature of the resistive heater based on the resistance of the resistive heater;
closing a first switch between a power supply and the sense resistor during the first time period; and
opening the first switch and closing a second switch between the power supply and the resistive heater during a second time period.

12. The method of claim 11, further comprising:
upon a condition that the temperature of the resistive heater is at or below a target temperature, (i) determining a heating voltage to be delivered to the resistive heater and (ii) delivering the heating voltage to the resistive heater, and upon a condition that the temperature of the resistive heater is above the target temperature, repeating the steps of claim 11.

13. The method of claim 12, wherein the steps of claim 11 are performed within the first time period, and delivering the heating voltage is performed within the second time period.

14. The method of claim 12, wherein delivering the heating voltage to the resistive heater includes pulse width modulating the heating voltage.

15. The method of claim 11, further comprising:
determining a heating voltage to be delivered to the resistive heater, and delivering the heating voltage to the resistive heater.

16. A non-transitory computer-readable medium including executable instructions that when executed by a processor cause the processor to perform the steps of claim 11.

17. A system to perform heating, comprising:
a sensing circuit;
a heating circuit;
a controller circuit;
a first switch between a power supply and a sense resistor of the sensing circuit; and
a second switch between the power supply and a resistive heating material of a heater of the heating circuit,
wherein the controller circuit controls power to the sensing circuit to determine a resistance value of the heater that is in both the sensing circuit and the heating circuit, the first switch is closed during a first time period, and during a second time period the first switch is opened and the second switch is closed.

18. The system of claim 17, wherein a temperature of the heater is determined based on the resistance value of the heater.

19. The system of claim 18, wherein upon a condition that the temperature of the heater is at or below a target temperature, the controller circuit determines a heating voltage to be delivered to the heater and delivers the heating voltage to the heater, and upon a condition that the temperature of the heater is above the target temperature, the controller circuit reduces the heating voltage to be delivered to the heater.

* * * * *